United States Patent [19]

Trenbeath et al.

[11] 4,377,530

[45] Mar. 22, 1983

[54] MANUFACTURE OF ISOCYANATES

[75] Inventors: Steven L. Trenbeath, Fairfield; Allan M. Feldman, Norwalk; Laurence J. Nummy, Stamford, all of Conn.

[73] Assignee: American Cyanamid Company, Stamford, Conn.

[21] Appl. No.: 354,997

[22] Filed: Mar. 5, 1982

[51] Int. Cl.$^3$ .......................................... C07C 118/00
[52] U.S. Cl. ................................................ 260/453 P
[58] Field of Search .................................... 260/453 P

[56] References Cited

U.S. PATENT DOCUMENTS 3,290,350  12/1966  Hoover ........................... 260/453 P

*Primary Examiner*—Dolph H. Torrence
*Attorney, Agent, or Firm*—Steven J. Hultquist

[57] ABSTRACT

A process for producing aromatic mono- and polyisocyanates by the addition reaction of isocyanic acid with vinyl aromatics is disclosed. The process is characterized by the slow addition of the olefin to a reaction mass of solvent and isocyanic acid to maintain the isocyanic acid in high excess to unreacted olefin.

7 Claims, No Drawings

MANUFACTURE OF ISOCYANATES

This invention relates to the manufacture of isocyanates by addition of isocyanic acid, HNCO, to olefins and in particular provides a process providing improved yields of isocyanates.

The addition reaction of isocyanic acid to olefins to obtain the corresponding isocyanate has been long known (U.S. Pat. No. 3,290,350). The reaction is especially useful in preparing isocyanates from vinyl aromatics. The reaction proceeds readily with addition of the isocyanate moiety to the more highly substituted carbon atom of the olefin.

The addition reaction of isocyanic acid to olefins can be used to prepare polyisocyanates as well as monoisocyanates. For example, meta- or para-diisopropenylbenzene can be reacted to produce both the monoisocyanate, isopropenyl $\alpha,\alpha$-dimethylbenzylisocyanate and the diisocyanate, tetramethylxylyenediisocyanate (TMXDI). Meta- and para-TMXDI are particularly useful for reaction with a wide variety of polyols to give polyurethanes which can be either rigid or flexible and which can be endowed with a wide variety of properties. Such polyurethanes can be formed into rigid and flexible foamed articles, sheets, high density sheets and articles of various shapes. The light stability of these polyurethanes makes them extremely useful in surface coatings and other applications where light stability is desirable, e.g., light stable RIM elastomers.

The addition reaction of isocyanic acid to olefins and particularly to diolefins suffers the disadvantage that the yields are poor and that large amounts of olefin and isocyanic acid are lost through self-polymerization. It is thus an important object of the present invention to provide a process for manufacture of isocyanates by the addition reaction of isocyanic acid to olefins in which the losses of olefin and of isocyanic acid are minimized and in which the yields of desired isocyanates are economically attractive.

This and other objects of this invention are basically achieved by controlling reaction pressure and temperature and by utilizing a large excess of isocyanic acid with the addition of the olefin slowly to the mass of isocyanic acid such that the amount of unreacted olefin in the reaction mass at any time is relatively low, that is, on the order of 1 part of olefin in the reaction mass to 25 to 100 parts or higher by weight of isocyanic acid.

In accordance with this invention the reaction is carried out in a solvent system utilizing sufficient solvent both for the olefin and isocyanic acid and for the resulting isocyanate. Generally the amount of solvent is such that the molarity of isocyanic acid is from about 1 to about 6. The use of solvents, of course, is well known and is described in U.S. Pat. No. 3,290,350. In accordance with this invention the preferred solvents are aromatic hydrocarbons, halogenated hydrocarbons, and aliphatic hydrocarbons such as toluene, chlorobenzene, heptane, benzene, methylene dichloride and the like. The solvent is introduced into the system in the initial reaction mass with the isocyanic acid. Additional solvent can be added with the olefin as it is added to the reaction mass. In addition some solvent can be introduced with the catalyst.

While the reaction will proceed without a catalyst, in order to obtain good yield in reasonable time a catalyst effective to promote the reaction should be employed. Such catalysts can be acid catalysts, as described in U.S. Pat. No. 3,290,350. Preferably, however, in accordance with this invention the catalyst is a sulfonic acid having a long alkyl chain or a hydrogen halide, such as hydrogen chloride, hydrogen bromide, or hydrogen iodide. In a system in which isocyanic acid is present there are inevitably present basic constituents, such as ammonia and cyamelide. These components react with acid catalysts removing them from solution as insoluble ammonium salts and the like. Thus in accordance with this invention sulfonic acid catalysts, such as dodecylbenzenesulfonic acid and dinonylnaphthalene sulfonic acid are preferably employed to insure the active components of the catalyst system remain in solution even though the ammonium salt or the like may be formed. Hydrogen halide catalysts are also effective catalysts.

As is known (East German Pat. Nos. 116,550 and 116,551), the presence of water interferes with the addition reaction of isocyanic acid to olefins. Even small amounts of water greatly reduce the yields of the isocyanate products. Thus in accordance with this invention the addition reaction is also preferably carried out at low water concentration, i.e., less than 200 to 300 parts per million.

In accordance with this invention the addition reaction is preferably carried out at substantially atmospheric pressure. While some subatmospheric pressure or some superatmospheric pressure, for example, $\frac{1}{2}$ or 2 atmospheres, is tolerable, most conveniently the reaction temperature is controlled in part by refluxing the reaction mixture, such that as a practical matter the reaction is at atmospheric pressure.

The reaction temperature is generally held in the range of 25° to 80° C. and preferably from 35° to 55° C. Temperature thus dictates that the solution should boil at the desired operating temperature in order to facilitate operation at atmospheric pressure. Similarly, the rate of addition of olefins is in part dictated by the desired operating temperature since the reaction is exothermic. The temperature range is dictated in part by the fact that there are competing reactions taking place. Polymerization of isocyanic acid is favored by higher temperatures, while olefin polymerization has been found to be favored by lower temperatures.

In the special case of reaction with polyolefins, such as the diisopropenylbenzenes, the reaction can be controlled to favor either production of the monoisocyanate or production of the diisocyanate by control of the molarity of the isocyanic acid in the reaction mixture. Generally isocyanic acid molarities above about 3, that is, from about 3 to 5 or 6 favor production of the diisocyanate while lower molarities, that is, from 3 down to about 1 favor production of the monisocyanate.

The reaction products are recovered by allowing the reaction mass to cool after which unreacted isocyanic acid is removed by distillation under reduced pressure or by entraining with a nitrogen stream. The reaction mass can then be filtered to remove solids, and solvent then is removed by distillation under reduced pressure. The products are then recovered by distillation or crystallization from hydrocarbon solvents.

Table I illustrates a series of examples of reaction of isocyanic acid and para-diisopropenylbenzene (DIPEB) to produce isopropenyl-$\alpha,\alpha$-dimethylbenzylisocyanate (TMI) and tetramethylxylylenediisocyanate (TMXDI). In the examples shown in Table I isocyanic acid in toluene (10–25 wt. percent) was charged into a reactor and warmed to reflux. Dodecylbenzene sulfonic acid catalyst was added and thereafter a solution of para-diisopropenylbenzene in toluene was added over a period of time. Samples of the reaction mass were taken from time to time, as indicated in Table I, and unreacted olefin and the yields of TMI and TMXDI were determined by vapor phase chromatography.

In Table I Examples 1-5 are arranged in descending ratio of HNCO to DIPEB, i.e., from about 20:1 on a molar basis in Examples 1 and 2, and 9:1 in Example 3 to 5:1 and 3:1 in Examples 4 and 5, respectively. HNCO molarity was about two to four in all five examples. As can be observed, reaction speed and yield are reduced as the relative proportion of HNCO is reduced.

Similar results have been obtained using aluminum chloride, aluminum iodide, hydrogen chloride, hydrogen bromide, hydrogen iodide, p-toluene sulfonic acid, tin (II) dibromide, ammonium dodecylbenzene sulfonate and a variety of other catalysts as well as with other solvents such as methylene chloride and chlorobenzene. Table II illustrates some of the variations in catalyst using toluene as solvent.

TABLE II

| EXAMPLE No. | Mole Ratios DIPEB = 1 HNCO | Mole Ratios DIPEB = 1 CAT | Init. HNCO Molarity | Init Temp. °C. | DIPEB Addition Time, Min | Time Min | Temp. °C. | Unreacted DIPEB | TMI | TMXDI | TOTAL |
|---|---|---|---|---|---|---|---|---|---|---|---|
| 6 | 9.8 | 0.09 HCl | 2.8 | 41 | 11 | 12 | 46 | 77.7 | 11.7 | — | 90.4 |
|   |   |   |   |   |   | 65 | 47 | 27.3 | 43.3 | 1.8 | 72.4 |
|   |   |   |   |   |   | 175 | 49 | 3.3 | 52.6 | 11.1 | 67.0 |
|   |   |   |   |   |   | 295 | 49 | 0.4 | 41.9 | 20.8 | 63.1 |
|   |   |   |   |   |   | 24hr | r.t. | 0.4 | 25.6 | 40.1 | 66.0 |
| 7 | 5.8 | 0.05 HBr | 3.0 | 38 | 145 | 160 | 45 | 11.7 | 38.3 | 25.3 | 75.3 |
|   |   |   |   |   |   | 190 | 45 | 5.9 | 38.2 | 26.9 | 72.0 |
|   |   |   |   |   |   | 250 | 45 | 0.7 | 35.0 | 35.1 | 70.8 |
|   |   |   |   |   |   | 310 | 45 | 0.3 | 28.6 | 39.8 | 68.7 |
|   |   |   |   |   |   | 365 | 45 | 0.8 | 23.9 | 44.0 | 68.7 |
|   |   |   |   |   |   | 665 | 45 | 0.2 | 12.1 | 55.2 | 67.5 |
|   |   |   |   |   |   | Inf. | 45 | 0.1 | 7.1 | 56.3 | 67.5 |
| 8 | 5.9 | 0.05 HBr | 3.0 | 23 | 310 | 315 | 24 | 10.6 | 34.1 | 22.5 | 67.2 |
|   |   |   |   |   |   | 365 | 24 | 4.5 | 36.2 | 24.7 | 65.4 |
|   |   |   |   |   |   | 425 | 24 | 1.7 | 35.6 | 27.3 | 64.6 |
|   |   |   |   |   |   | 1445 | 24 | — | 12.8 | 46.0 | 58.8 |
|   |   |   |   |   |   | 1865 | 24 | — | 8.0 | 49.6 | 57.7 |
|   |   |   |   |   |   | 2835 | 24 | — | 4.8 | 53.0 | 57.8 |
| 9 Meta-DIPEB | 7 | 0.06 HBr | 3.0 | 22 | 370 | 375 | 25 | 39.1 | 37.3 | 10.3 | 86.7 |
|   |   |   |   |   |   | 410 | 25 | 35.8 | 38.6 | 10.6 | 85.0 |
|   |   |   |   |   |   | 1370 | 25 | 3.1 | 45.0 | 29.0 | 77.1 |
| 10 | 5.9 | 0.05 para toluene sulfonic acid | 2.9 | 25 | 312 | 317 | 25 | 17.8 | 37.8 | 22.3 | 77.9 |
|   |   |   |   |   |   | 387 | 25 | 8.2 | 41.8 | 24.8 | 74.8 |
|   |   |   |   |   |   | 457 | 25 | 5.0 | 42.1 | 26.9 | 74.0 |
|   |   |   |   |   |   | 1350 | 25 | 0.3 | 30.7 | 37.6 | 68.6 |
| 11 | 9.7 | 0.05 Ammonium Dodecyl- benzene sulfonate | 1.7 | 52 | 215 | 230 | 52 | 13.5 | 67.1 | 9.9 | 90.5 |
|   |   |   |   |   |   | 330 | 52 | 1.3 | 60.5 | 24.0 | 85.8 |
|   |   |   |   |   |   | 510 | 52 | 0.6 | 48.2 | 34.2 | 83.0 |
| 12 | 4.1 | 0.05 HBr | 1.3 | 50 | 260 | 275 | 50 | 56.7 | 32.9 | 1.6 | 91.2 |
|   |   |   |   |   |   | 335 | 50 | 48.4 | 37.1 | 1.9 | 87.4 |
|   |   |   |   |   |   | 400 | 50 | 44.3 | 42.1 | 2.2 | 88.6 |
| 13 | 7.3 | 0.06 HI | 3.0 | 31 | 231 | 250 | 40 | — | 4.2 | 42.2 | 46.4 |

*determined by vapor phase chromotography

EXAMPLE 14

Following the general procedure outlined with respect to the previous Examples 29.7 m.moles DIPEB was reacted with 189.4 m.moles HNCO using 3.2

TABLE I

| Example No. | Reactants, m.moles HNCO | Reactants, m.moles DIPEB | Reactants, m.moles CAT | Wt. Reaction Mass, g. | Init. Temp. °C. | DIPEB Addition time, min. | Time, min. | Temp °C. | Unreacted DIPEB | TMI | TMXDI | TOTAL |
|---|---|---|---|---|---|---|---|---|---|---|---|---|
| 1. | 204 | 10.1 | 1 | 55.3 | 41 | 14 | 19 | 44 | 0.8 | 44.7 | 54.6 | 100.1 |
|   |   |   |   |   |   |   | 37 | 44 | 0.4 | 28.5 | 69.9 | 98.8 |
|   |   |   |   |   |   |   | 168 | 44 | — | 10.2 | 89.0 | 99.2 |
| 2. | 195 | 10.1 | 1 | 91.3 | 50 | 33 | 38 | 55 | 7.8 | 64.4 | 22.4 | 94.6 |
|   |   |   |   |   |   |   | 53 | 55 | 1.7 | 58.8 | 32.5 | 93.0 |
|   |   |   |   |   |   |   | 128 | 57 | 0.4 | 33.3 | 63.3 | 97 |
| 3. | 89 | 10.1 | 1 | 48 | 53 | 26 | 32 | 54 | 11.5 | 61.4 | 17.9 | 90.8 |
|   |   |   |   |   |   |   | 87 | 54 | 1.6 | 52.2 | 37.8 | 91.6 |
|   |   |   |   |   |   |   | 252 | 55 | 1.7 | 43.5 | 46.1 | 91.3 |
| 4. | 103 | 20.3 | 2 | 54.8 | 51 | 6 | 15 | 61 | 5.1 | 56.4 | 19.1 | 80.6 |
|   |   |   |   |   |   |   | 128 | 54 | 2.7 | 47.9 | 30.2 | 80.8 |
|   |   |   |   |   |   |   | 320 | 53 | 2.9 | 44.6 | 29.9 | 77.4 |
| 5. | 61 | 20.3 | 1 | 35.5 | 52 | 18 | 28 | 53 | 19.9 | 47.6 | 9.2 | 76.7 |
|   |   |   |   |   |   |   | 50 | 53 | 13.8 | 50.9 | 10.8 | 75.5 |
|   |   |   |   |   |   |   | 300 | 52 | 9.3 | 49.7 | 12.6 | 71.6 |

*determined by vapor phase chromatography m.moles HBr as catalyst. The solvent was methylene chloride, and the total weight of the reaction mass was 83.3 g. The reaction conditions and results are shown in Table III.

EXAMPLE 15

Following the procedure of Example 14 191 m.moles HNCO were reacted with 31.4 m.moles DIPEB in chlorobenzene using 2 m.moles HCl catalyst. The total weight of the reaction mass was 72.4 g. The reaction condition and results are shown in Table III.

EXAMPLE 16

Following the procedure of Example 14 108 m.moles HNCO were reacted with 12.4 m.moles of TMI in toluene using 0.5 m.moles HBr catalyst. The total weight of the reaction mass was 33.4 g. The reaction condition and results are shown in Table III.

tion mass of isocyanic acid and inert solvent therefor at approximately atmospheric pressure and at a temperature between about 25° and 80° C. and adding the olefin to the reaction mass at a rate such that the molar proportion of remaining isocyanic acid to unreacted olefin is above about 25 to 1, while maintaining said temperature between 25° and 80° C. and maintaining the molarity of unreacted isocyanic acid in said mass between about 1 and about 6.

2. The improvement according to claim 1 in which said olefin is a diisopropenylbenzene.

3. The improvement according to claim 1 or claim 2 in which said solvent is toluene.

4. The improvement according to claim 1 or claim 2 in which said solvent is methylene chloride.

5. The improvement according to claim 1 or claim 2 in which said solvent is chlorobenzene.

6. The improvement according to claim 1 or claim 2 in which said catalyst is dodecylbenzene sulfonic acid.

7. The improvement according to claim 1 or claim 2 in which said catalyst is selected from hydrogen chloride and hydrogen bromide.

TABLE III

| Example No. | Initial Temp. °C. | Olefin Addition Time, Min. | Yield Based on Olefin, %* | | | | |
|---|---|---|---|---|---|---|---|
| | | | Time Min | Temp. °C. | Unreacted Olefin | TMI | TMXDI | TOTAL |
| 14 | 32 | 165 | 180 | 32 | — | 7.4 | 25.9 | 33.3 |
| | | | 210 | 34 | — | 5.1 | 27.6 | 32.7 |
| | | | 285 | 34 | — | 2.2 | 30.0 | 32.2 |
| | | | 345 | 34 | — | 1.3 | 30.8 | 32.1 |
| | | | 1440 | 25 | — | 0.2 | 32.1 | 32.3 |
| 15 | 35 | 295 | 310 | 38 | 4.4 | 31.4 | 13.3 | 49.1 |
| | | | 370 | 38 | 1.2 | 30.2 | 15.6 | 47.0 |
| | | | 1360 | 27 | — | 14.5 | 28.7 | 43.2 |
| | | | Inf. | 28 | — | — | — | — |
| 16 | 39 | 180 | 185 | 42 | n.a | 72.1 | 28.1 | 100.2 |
| | | | 215 | 42 | " | 68.1 | 30.2 | 98.3 |
| | | | 305 | 42 | " | 57.5 | 37.1 | 94.6 |
| | | | 365 | 42 | " | 53.5 | 45.3 | 98.8 |
| | | | 1350 | 27 | " | 41.9 | 54.4 | 96.3 |
| | | | Inf. | 27 | " | 12.3 | 77.6 | 89.9 |

*determined by vapor phase chromatography

We claim:

1. In the preparation of isocyanates by addition of isocyanic acid to an olefin in an inert solvent and in the presence of a catalyst effective to promote the reaction, the improvement which comprises establishing a reac-

* * * * *